US United States Patent [19] [11] 4,294,828
Thominet et al. [45] Oct. 13, 1981

[54] NEW DERIVATIVES OF 4-AMINO-5-ALKYL SULPHONYL ORTHOANISAMIDES, METHODS OF PREPARING THEM AND THEIR APPLICATION AS PSYCHOTROPIC AGENTS

[75] Inventors: Michel Thominet, Paris; Jacques Acher, Itteville; Jean-Claude Monier, Lardy, all of France

[73] Assignee: Societe d'Etudes Scientifiques et Industrielles de l'Ile de-France, Paris, France

[21] Appl. No.: 4,397

[22] Filed: Jan. 18, 1979

[30] Foreign Application Priority Data

Jan. 20, 1978 [FR] France ................................. 78-01632

[51] Int. Cl.³ ..................... A61K 31/40; A61K 31/62; C07D 207/08

[52] U.S. Cl. ............................... 424/232; 260/326.47; 562/430; 564/162; 564/510; 424/274

[58] Field of Search .................... 260/326.47; 424/274, 424/232

[56] References Cited

U.S. PATENT DOCUMENTS

| | | | |
|---|---|---|---|
| 3,342,826 | 9/1967 | Miller et al. | 260/326.47 |
| 3,862,139 | 1/1975 | Podesva et al. | 260/326.47 |
| 3,975,434 | 8/1976 | Bulteau et al. | 260/326.47 |
| 4,021,567 | 5/1977 | Kaplan et al. | 260/326.47 |

*Primary Examiner*—Alton D. Rollins
*Attorney, Agent, or Firm*—Omri M. Behr

[57] ABSTRACT

There are provided certain N-(1-lower alkyl-2-pyrrolidylmethyl)2-lower alkoxy-4-amino-5-lower alkyl sulphonyl benzamides and derivatives thereof which provide surprising antiapomorphine and antiserotonin activity.

3 Claims, No Drawings

NEW DERIVATIVES OF 4-AMINO-5-ALKYL SULPHONYL ORTHOANISAMIDES, METHODS OF PREPARING THEM AND THEIR APPLICATION AS PSYCHOTROPIC AGENTS

BACKGROUND OF THE INVENTION

The compounds of the present invention fall within the general disclosure of U.S. Pat. No. 3,342,826. It should be noted however that none of the compounds prepared in said patent nor the specifically named benzoic acids utilized for preparing the prior art compounds contain the 4-amino-5-lower alkylsulphonyl benzoyl moiety.

The disclosure of utility set forth in column 1 lines 33 through 43 of the prior art patent make no mention whatsoever of the surprising antiapomorphine and antiserotonin activities of the compounds of the present invention.

The prior art patent is assigned to Applicant's assignee.

SUMMARY OF THE INVENTION

There are provided novel compounds having antiapomorphine and antiserotonin activity.

A novel compound of the present invention have the formula:

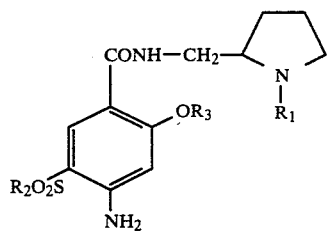

wherein $R_1$ is lower alkyl of 1 to 5 carbon atoms or lower alkenyl of 2 to 5 carbon atoms, $R_2$ and $R_3$ are lower alkyl of 1 to 5 carbon atoms.

The novel compounds of the present invention also include the N-oxides, the quaternary ammonium salts and the salts with pharmacologically acceptable acids of the foregoing compounds. The dextrorotatory and levorotatory isomers of all of the foregoing are also included within the scope of the invention.

The compounds of the present invention are readily prepared by either of two routes, the appropriate 2-alkoxy-4-amino-5-mercaptobenzoic acid is treated with a lower alkyl sulphate to provide the corresponding 5-lower alkylthiobenzoic acid which is then oxidized to provide the 2-alkoxy-4-amino-5-alkylsulphonyl benzoic acid of the formula:

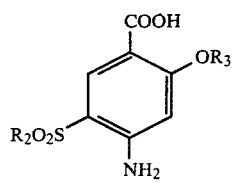

The acid II is then reacted with an amine of the formula:

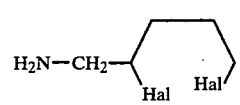

the reaction is carried out by activating either the acid moiety or the amino moiety by means known in the art. Thus the acid moiety may be converted into the corresponding acyl halide, alkyl ester, reactive ester, aryl ester, N-hydroxy imide ester, symmetrical anhydride, or mixed anhydride with an ester of a carbonic acid or a haloformic ester, azide, hydrazide, azolide, acid isothiocyanate, trichloroacetophenone, or triphenylphosphine derivative.

Alternatively, the acid moiety is left intact and the amine activated by reaction with phosphorus chloride, phosphorus oxychloride, a dialkyldiaryl-, or orthophenylenechlorophosphite, an alkyl- or aryldichlorophosphite, or the formation of an isothiocyanate of the amine or a substituted urea or sulphamide.

The activated compound is then reacted with the unactivated component by means well-known in the art.

In a further embodiment the free acid and the free amine may be reacted together in the presence of a condensing agent such as, for example, silicon tetrachloride, trichlorophenylsilane, phosphoric anhydride, a carbodiimide or an alkoxyacetylene.

In yet another embodiment of this synthetic procedure of the present invention there is provided a dihaloalkylamine of the formula:

$$H_2N-CH_2-\overset{Hal\quad Hal}{\diagup\!\!\!\diagdown} \qquad (IV)$$

the dihaloalkylamine (IV) is then reacted with an acid of formula (II) as above or one of its active derivatives again as defined above to provide a compound of the formula:

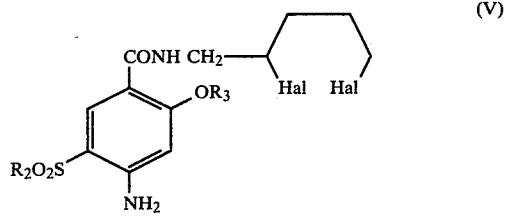

The compound of formula (V) is then reacted with a primary amine of the formula:

$$H_2N-R_1 \qquad (VI)$$

The thus produced compounds of the present invention may be reacted with pharmaceutically acceptable acids to yield acid addition salts; with alkyl halides or alkyl sulphates to give the corresponding quaternary ammonium salts; or oxidized with the usual oxidizing agents to provide the corresponding N-oxide.

DESCRIPTION OF THE PREFERRED EMBODIMENTS

Especially preferred among the compounds of the present invention are the compounds of formula I, wherein $R_1$ is methyl, ethyl, propyl, allyl, $R_2$ is methyl, ethyl, propyl, or isopropyl, $R_3$ is methyl.

Among the pharmaceutically acceptable acids which form salts with the compounds of formula I may be mentioned inclusively but not in a limiting manner, inorganic or organic acids such as hydrochloric, hydrobromic, sulphuric, phosphoric, oxalic, acetic, tartaric, citric, or methane sulphonic acid.

The method of activating compounds of formula II in order to react them with compounds of formula III and of activating compounds of formula III to react them with compounds of formula II are well-known in the art. The amidation reaction may be carried out either by mixing the reactant in situ or, if desired, after previously separating the intermediate reactants.

In the second embodiment of the procedure wherein an acid formula II is reacted with a dihaloalkylamine the amidation reaction may be carried out with or without a solvent. It has however, been found useful to carry out the reaction utilizing either inert solvents or an excess of the haloalkylamine as the solvent. In both cases the reaction is most suitably carried out under solvent reflux although the procedure is by no means limited thereto.

As inert solvents for the amidation reaction there may be mentioned alcohols, poly ols, ketones, benzene, toluene, dioxane, chloroform or diethylene glycol dimethyl-ether.

The N-oxides of the present invention may be prepared in the usual manner by reacting with suitable oxidizing agent such as hydrogen peroxide and magnesium dioxide.

PHARMACOLOGICAL DATA

The acute toxicity of the compounds according to the invention has been studied in mice. The lethal doses 50 are set out in the table which follows:

| | LD$_{50}$ DETERMINED IN THE MALE MOUSE - EXPRESSED IN mg/kg | | | |
|---|---|---|---|---|
| Compounds | Intravenous | I.P. | Subcutaneous | Oral |
| 1 | 56–60 | 175–180 | 224–250 | 1024–1054 |
| 2 | 56–57 | 210–217 | 280 | 1326–1330 |
| 3 | 106–107 | 216–217 | 312–330 | 2232–2375 |
| 4 | 39.8 | 188 | 254–263 | 1564–1621 |
| 5 | 44.8 | 122–128 | 137–149 | 1109–1160 |
| 6 | 62–64 | 304–322 | 380–396 | 1186–1260 |
| 7 | 43–46.8 | 160–165 | 140–144 | 570–629 |
| 8 | 46.5–50 | 234–238 | 208–225 | 625–660 |
| 9 | 54 | 200–216 | 202.5 | 996–105 |

1: N-(1-ethyl-2-pyrrolidylmethyl)-2-methoxy-4-amino-5-ethylsulphonylbenzamide
2: N-(1-methyl-2-pyrrolidylmethyl)-2-methoxy-4-amino-5-ethylsulphonylbenzamide
3: N-(1-allyl-2-pyrrolidylmethyl-2-methoxy-4-amino-5-ethylsulphonylbenzamide
4: dextrorotatory N(1-ethyl-2-pyrrolidylmethyl)-2-methoxy-4-amino-5-ethylsulfonyl benzamide tartrate
5: levorotatory N(1-ethyl-2-pyrrolidylmethyl)-2-methoxy-4-amino 5-ethylsulphonyl benzamide tartrate
6: dextrorotatory N-(1-methyl 2-pyrrolidylmethyl) 2-methoxy 4-amino 5-ethylsulfonyl benzamide
7: N(1-ethyl 2-pyrrolidylmethyl) 2-methoxy 4-amino 5-propylsulphonyl benzamide.
8: N-(1-ethyl 2-pyrrolidylmethyl) 2-methoxy 4-amino 5-methylsulphonyl benzamide.
9: N-(1-methyl 2-pyrrolidylmethyl) 2-methoxy 4-amino 5-methylsulphonyl benzamide.

The cataleptic action has been studied as follows.

Benzamides are administered subcutaneously to male rats. The criterion taken for the cataleptic state is that the animal should be immobile for 30 seconds with its rear limbs apart, arranged carefully on wooden cubes 4 cm high, which thus puts the animal in an unaccustomed and uncomfortable position.

The cataleptic action is measured when the effect is at its maximum, i.e. 5 to 7 hours after the substance has been administered.

With a dose of 200 mg/kg given subcutaneously, benzamides 1 to 4 and 6 to 8 are found to have absolutely no cataleptic action, and compound 5 is found to produce a cataleptic state in only 30% of the animals, after 7 hours.

The compounds of the invention have undergone other pharmacodynamic tests, and in particular their antiemetic power relative to apomorphine has been measured.

The test has been carried out on dogs by the method of Chen and Ensor.

The compounds of the invention are administered subcutaneously, 30 minutes before the apomorphine, which is administered subcutaneously in a dose of 100 μg/kg.

The results obtained are as follows:

| Antiapomorphine ED$_{50}$ in the dog expressed in μg/kg/s.c. | | | | | | | | | |
|---|---|---|---|---|---|---|---|---|---|
| Compound | 1 | 2 | 3 | 4 | 5 | 6 | 7 | 8 | 9 |
| ED$_{50}$ | 0.29 | 0.8 | 0.65 | 12 | 0.28 | 8 | 1.6 | 2.7 | 7 |

The results of this test, which prove an antagonism to apomorphine 5 to 20 times greater than that of known compounds in the same series, have led us to think that the compounds according to the invention have a strong action on the central nervous system. The pharmacodynamic study of the compounds of the invention was concluded with antiserotonin tests inter alia in connection with stomach ulceration in the rat and bronchospasm in the guinea-pig.

The antiserotonin action in connection with stomach ulceration has been studied in the rat under the following conditions:

30 mg/kg of serotonin is administered subcutaneously to female rats in two stages, with an interval of 16 hours. The product being studied is administered subcutaneously at the same time as the serotonin, in two stages with increasing doses. A group of 30 animals is used for each dose and a group of 60 animals is used as the control. The animals are sacrificed 22 hours after the first injection of serotonin, and their stomachs are taken out and examined. The percentage protection for each dose studied is determined, then the DE$_{50}$, the dose protecting 50% of the animals, from gastric ulceration, is measured graphically.

The results obtained are as follows:

| Antiserotonin ED$_{50}$ in respect of stomach ulceration, in the rat - expressed in mg/kg/s.c. | | | | | | | |
|---|---|---|---|---|---|---|---|
| Compound | 1 | 2 | 3 | 4 | 6 | 7 | 8 | 9 |
| ED$_{50}$ | 1 | 0.4 | 0.65 | 0.46 | 0.34–0.44 | 3.2 | 3 | 1.14 |

The antiserotonin action in respect of bronchospasm has been studied in the guinea-pig under the following conditions:

The bronchospasm is recorded by the method of Konzett and Rossler, which comprises connecting the trachea of the guinea-pig to an artificial respiration pump, which passes a constant volume of air, slightly greater than the respiratory capacity of the animal, into the bronchi at a physiological rhythm. The excess quantity of air, which varies according to the diameter of the bronchi, is discharged to a special manometric device which measures the volume of air at each inhalation.

The sero tonin is administered intravenously to the guinea-pigs in a dose of 20 μg/kg. The guinea-pigs have previously been anaesthetised with ethyl carbamate, thus producing a bronchial spasm.

The product to be studied is then administered intravenously, after which the administration of sero tonin is repeated one minute later. The percentage inhibition of bronchospasm is measured for each dose of the product to be studied, then the antiserotonin DE$_{50}$ relative to bronchospasm in the guinea-pig is determined.

The results obtained are as follows:

| Antiserotonin ED$_{50}$ relative to bronchospasm in the guinea-pig - expressed in μg/kg/IV | | |
|---|---|---|
| COMPOUND | 1 | 4 |
| ED$_{50}$ | 74 | 106 |

These antiserotonin properties very clearly distinguish the compounds of the invention from sulpiride, for which the antiserotonin ED$_{50}$ relative to stomach ulceration in the rat is 110 mg/kg.

The low toxicity of the compounds according to the invention and the absence of any undesirable side effects such as catalepsy, which normally accompany this type of product, have made it possible to proceed to clinical tests. These have revealed powerful psychotropic properties of the compounds according to the invention, as follows (their originality has to do with the combination of antiapomorphine and antiserotonin properties, which is surprising at this degree in the benzamide series):
—effect of removing inhibitions; in particular this makes it the preferred treatment for autism
—treatment for sudden attacks of delirium
—antimigraine action In addition, these derivatives have proved valuable in weaning drug addicts.

Because of their psycho stimulating properties they reduce the danger of relapse during the deficiency period which follows weaning. They are not addictive.

Finally, the sedative effect is zero: these derivatives are not recommended for acute psychoses with agitation.

Clinical studies carried out on several hundred patients taking daily doses of 50 to 750 mg have brought out the therapeutic properties of the compounds according to the invention and shown that they can be tolerated extremely well.

Thus for example, 200 mg per day of compound (1) was administered orally or by intramuscular injection to 30 patients who were alcoholic or heroin addicts. In 28 cases the product acted rapidly and the drug addicts asked for more. Its effect is different from that of opiates and the main antalgics. The patients did not suffer any dependency syndrome when the treatment was suddenly stopped. No neurological side effect was observed.

41 patients suffering from sudden attacks of delirium were treated with 350 mg per day of compound (2), administered orally or by intramuscular injection. In 38 cases a very good antipsychotic action was observed in the sudden attacks of delirium; there was an antidepressive action and excellent tolerance in all cases.

21 patients suffering from catatonic hebephrenia were treated with compound (1), a daily dose of 100–300 mg being given orally or by intramuscular injection. In 13 cases removal of inhibitions was observed, sometimes with a reversal of mood, which made it possible to make contact with the patient.

Compound (1) was administered in a dose of three tablets per day (300 mg) to a patient suffering from frequent migraines; these obliged her to interrupt any professional activity for three or four days per month. The migraines decreased from the first month and disappeared altogether from the second month, with a continuous dosage of only one tablet per day (100 mg).

Compound (1) was administered in a daily dose of 300 mg taken in three portions, to two twin brothers who suffered each month from attacks of migraine accompanied by vomiting. For one of the twins the migraine disappeared immediately. For the other the pain disappeared from the second month and only a few attacks of nausea persisted.

Compound (2) was administered continuously, in doses of two tablets per day (200 mg), to a woman who had suffered from attacks of migraine for four years. The attacks had not responded to curative treatment (ergotamine and caffeine) or preventive treatment. The attacks are becoming rare (1 or 2 per month instead of 10 to 15), their intensity is decreasing and they can regularly be dealt with by taking two tablets of ergotamine and caffeine.

Compound (2) was administered in doses of three tablets per day (300 mg) to a woman suffering from quasi permanent occipital cephalalgia and several times a week from attacks of migraine with right hemicrania, photophobia and nausea. From the third week the migraine attacks disappeared completely.

EXPERIMENTAL

In order to illustrate the technical features of the invention some examples will now be described. It should be made clear that the invention is not restricted to these, either in respect of the method used or the possible applications.

EXAMPLE 1

N-(1-ethyl 2-pyrrolidylmethyl) 2-methoxy 4-amino 5-ethylsulphonyl benzamide 2-methoxy 4-amino 5-ethylthiobenzoic acid 159 g of 2-methoxy 4-amino 5-mercaptobenzoic acid, 355 cm$^3$ of water and 160 cm$^3$ of caustic soda solution are placed in a flask fitted with a condenser. The mixture is heated until the solid dissolves, then 123 g of ethyl sulphate is added. The mixture is heated to reflux, treated with 10 cm³ of 30% caustic soda solution, then heated to reflux for 1 hour. After cooling, 800 cm³ of water is added and the solution is filtered. The precipitate obtained by adding 100 cm³ of concentrated hydrochloric acid in the presence of ether is drained, washed with water and dried.

162 g of 2-methoxy 4-amino 5-ethylthio benzoic acid is obtained (yield=88%).

2-methoxy 4-amino 5-ethylsulphonyl benzoic acid 123 g of 2-methoxy 4-amino 5-ethylthiobenzoic acid is dissolved hot in 542 cm³ of acetic acid. The solution obtained is cooled to 35° C., then 185 cm³ of 131 vol. hydrogen peroxide is added in small quantities while the temperature is raised to 80° C.

The temperature is lowered to 40° C. and the mixture is kept at that temperature for some hours then cooled to 10° C.

The precipitate formed is drained, washed with acetic acid and dried, then dissolved in 600 cm³ of water and 100 cm³ of 20% ammonia.

The precipitate formed by adding 70 cm³ of concentrated hydrochloric acid is cooled, drained, washed with water and dried.

61.5 g of 2-methoxy 4-amino 5-ethylsulphonyl benzoic acid hydrate is obtained (yield 42% - M.P. 95°–100° C.).

N-(1-ethyl 2-pyrrolidylmethyl) 2-methoxy 4-amino 5-ethylsulphonyl benzamide 81 g of 2-methoxy 4-amino 5-ethylsulphonyl benzoic acid and 297 cm³ of acetone are placed in a flask fitted with an agitator, a thermometer and a dropping funnel, followed by 33 g of triethylamine. The solution is cooled to 0° C., then 30 g of ethyl chloroformate is added drop by drop between 0° and 5° C.

When the mixture has been agitated 51 g of 1-ethyl 2-amino methyl pyrrolidine is added drop by drop between 5° and 10° C. The mixture is agitated at 10° C. then at ambient temperature. The triethylamine hydrochloride which precipitates is drained, then the acetone is distilled. The residue is dissolved in 600 cm³ of water in the presence of caustic soda solution. The base crystallises after seeding and is drained, washed with water and dried.

When the crystals have been purified by passing them through hydrochloride and re-crystallising them in acetone, 66 g of N-[1-ethyl 2-pyrrolidylmethyl] 2-methoxy 4-amino 5-ethylsulphonyl benzamide is obtained (yield 61%-M.P.=126° to 127° C.).

EXAMPLE II

N-[1-methyl 2-pyrrolidylmethyl] 2-methoxy 4-amino 5-ethylsulphonyl benzamide 144 g of 2-methoxy 4-amino 5-ethylsulphonyl benzoic acid, 440 cm³ of acetone and 44.5 g of triethylamine are placed in a flask fitted with an agitator, a thermometer and a dropping funnel. The solution is cooled to 0° C., then 48 g of ethyl chloroformate is added drop by drop between 0° and 15° C.

The mixture is agitated for 30 minutes between 0° and 5° C., then 67 g of 1-methyl 2-aminomethylpyrrolidine is added drop by drop between 5° and 10° C. The mixture is then agitated firstly at 10° C. then at room temperature. The product obtained is drained, washed with acetone, treated with 500 cm³ of water, then drained, washed with water and dried.

The substance obtained is re-crystallised in absolute alcohol and purified by passing it through hydrochloride. After further re-crystallisation in absolute alcohol, 101 g of N-[1-methyl 2-pyrrolidylmethyl] 2-methoxy 4-amino 5-ethylsulphonyl benzamide is obtained (yield=157°–158° C.).

EXAMPLE III

N-[1-allyl 2-pyrrolidylmethyl] 2-methoxy 4-amino 5-ethylsulphonyl benzamide 132 g of 2-methoxy 4-amino 5-ethylsulphonyl benzoic acid, 510 cm³ acetone and 51.5 g of triethylamine are placed in a flask fitted with an agitator, a thermometer and a dropping funnel. The solution obtained is cooled to 0° C., then 55.5 g of ethyl chloroformate is added drop by drop, between 0° and 5° C.

The mixture is agitated for 30 minutes at 5° C., then 96 g of 1-allyl 2-aminoethylpyrrolidine is added drop by drop, between 5° and 10° C. The mixture is agitated at 10° C. then at room temperature.

The triethylamine hydrochloride which is precipitated is drained and washed with acetone, then the acetone is distilled. The residue is dissolved in water and 60 cm³ of concentrated hydrochloric acid, then the solution obtained is filtered and treated with the 30% caustic soda solution. The oil formed is extracted with methylene chloride, then the organic solution is dried over potassium carbonate and the methylene chloride is distilled.

After purification 131 g of N-[1-allyl 2-pyrrolidyl methyl] 2-methoxy 4-amino 5-ethylsulphonyl benzamide is obtained (yield=67%-M.P.111°–112° C.).

EXAMPLE IV

Dextrorotatory tartrate of N-[1-ethyl 2-pyrrolidylmethyl] 2-methoxy 4-amino 5-ethylsulphonyl benzamide Dextrorotatory N-[1-ethyl 2-pyrrolidylmethyl] 2-methoxy 4-amino 5-ethylsulphonyl benzamide Following the same procedure as in Example I, 95 g of 2-methoxy 4-amino 5-ethylsulphonyl benzoic acid dissolved in 370 m of acetone, in the presence of 37 g of triethylamine, is treated with 40 g of ethyl chloroformate then with 57 g of dextrorotatory 1-ethyl 2-aminomethylpyrrolidine.

115 g of dextrorotatory N-[1-ethyl 2-pyrrolidyl methyl] 2-methoxy 4-amino 5-ethylsulphonyl benzamide is obtained (yield=84%).

Dextrorotatory tartrate of N-1-ethyl 2-pyrrolidylmethyl 2-methoxy 4-amino 5-ethylsulphonyl benzamide 133 g of dextrorotatory N-[1-ethyl 2-pyrrolidyl methyl] 2-methoxy 4-amino 5-ethylsulphonyl benzamide is dissolved in 500 ml of methanol, then 54 g of dextrorotatory tartaric acid dissolved in 80 ml of methanol is added. The crystals which form after seeding are drained, washed with methanol then dried.

After re-crystallisation in methanol, 106 g of dextrorotatory tartrate of N-[1-ethyl 2-pyrrolidylmethyl] 2-methoxy 4-amino 5-ethylsulphonyl benzamide is obtained (yield=56%-N.P.=98°–108° C.-[α]20° C. in 5% aqueous solution=+7°, 5).

EXAMPLE V

Levorotatory tartrate of N-[1-ethyl 2-pyrrolidylmethyl] 2-methoxy 4-amino 5-ethylsulphonyl benzamide

*Levorotatory N-[1-ethyl 2-pyrrolidylmethyl] 2-methoxy 4-amino 5-ethylsulphonyl benzamide*

Following the same procedure as in Example I, 104 g of 2-methoxy 4-amino 5-ethylsulphonyl benzoic acid dissolved in 380 ml of acetone, in the presence of 38 g of triethylamine, is treated with 41 g of ethyl chloroformate then with 58 g of levorotatory 1-ethyl 2-aminomethyl pyrrolidine.

140 g of levorotatory N[1-ethyl 2-pyrrolidylmethyl] 2-methoxy 4-amino 5-ethylsulphonyl benzamide is obtained (yield 100%).

*Levorotatory tartrate of N-[1-ethyl 2-pyrrolidylmethyl] 2-methoxy 4-amino 5-ethylsulphonyl benzamide*

136 g of levorotatory N-[1-ethyl 2-pyrrolidylmethyl] 2-methoxy 4-amino 5-ethylsulphonyl benzamide is dissolved in 500 ml of methanol, then 58 g of levorotatory tartaric acid dissolved in 70 m of methanol is added. The crystals formed are drained, washed with methanol and dried.

After re-crystallisation in methanol, 103 g of levorotatory tartrate of N-[1-ethyl 2-pyrrolidylmethyl] 2-methoxy 4-amino 5-ethylsulphonyl benzamide is obtained (yield=54%; M.P.=100° C.; [α]20° C. in 5% aqueous solution=−6°, 3).

EXAMPLE VI

Dextrorotatory N-1-methyl 2-pyrrolidylmethyl 2-methoxy 4-amino 5-ethylsulphonyl benzamide

Following the same procedure as in Example I, 117 g of 2-methoxy 4-amino 5-ethylsulphonyl benzoic acid dissolved in 450 ml of acetone, in the presence of 46 g of triethylamine, is treated with 49 g of ethyl chloroformate then with 69 g of dextrorotatory 1-methyl 2-aminomethylpyrrolidine.

69 g of dextrorotatory N-1-methyl 2-pyrrolidylmethyl 2-methoxy 4-amino 5-ethylsulphonyl benzamide is obtained (yield=44%-M.P.=125°-126° C.−[α]20° C. in a 5% dimethylformamide solution=+35.3°).

EXAMPLE VII

N-(1-methyl 2-pyrrolidylmethyl) 2-methoxy 4-amino 5-propylsulphonyl benzamide

*2-methoxy 4-amino 5-propylthio benzoic acid*

Following the same procedure as in example I and starting with 2-methoxy 4-amino 5-mercapto benzoic acid, 2-methoxy 4-amino 5-propylthio benzoic acid is obtained (M.P.=104°-105° C.).

*2-methoxy 4-amino 5-propylsulphonyl benzoic acid*

Following the same procedure as in Example I, 137 g of 2-methoxy 4-amino 5-propylthio benzoic acid dissolved in 570 ml of acetic acid is treated with 233 ml of 110 vol. hydrogen peroxide.

108 g of 2-methoxy 4-amino 5-propylsulphonyl benzoic acid is obtained (yield=69%-N.P.=165°-166° C.).

*N-(1-ethyl 2-pyrrolidylmethyl) 2-methoxy 4-amino 5-propylsulphonyl benzamide.*

Following the same procedure as in Example I, 160 g of 2-methoxy 4-amino 5-propylsulphonyl benzoic acid dissolved in 590 ml of acetone, in the presence of 59 g of triethylamine, is treated with 64 g of ethyl chloroformate then with 101 g of 1-ethyl 2-aminomethylpyrrolidine.

After purification, 151 g of N-[1-ethyl 2-pyrrolidylmethyl] 2-methoxy 4-amino 5-propylsulphonyl benzamide is obtained (yield=67%-M.P.=105°-106° C.).

EXAMPLE VIII

N-[1-methyl 2-pyrrolidylmethyl] 2-methoxy 4-amino 5-methylsulphonyl benzamide

*2-methoxy 4-amino 5-methylthio benzoic acid*

Following the same procedure as in Example I and starting with 2-methoxy 4-amino 5-mercapto benzoic acid, 2-methoxy 4-amino 5-methylthio benzoic acid is obtained (M.P.=151°-152° C.).

*2-methoxy 4-amino 5-methylsulphonyl benzoic acid*

Following the same procedure as in Example I, 158 g of 2-methoxy 4-amino 5-methylthio benzoic acid dissolved in 742 ml of acetic acid is treated with 310 ml of 110 vol. hydrogen peroxide.

114.5 g of 2-methoxy 4-amino 5-methylsulphonyl benzoic acid is obtained (yield=63%-M.P.=178°-180° C.).

*N-(1-methyl 2-pyrrolidylmethyl) 2-methoxy 4-amino 5-methylsulphonyl benzamide*

Following the same procedure as in Example I, 131 g of 2-methoxy 4-amino 5-methylsulphonyl benzoic acid dissolved in 538 ml of acetone, in the presence of 54 g of triethylamine, is treated with 58.5 g of ethyl chloroformate then with 73 g of 1-methyl 2-aminomethylpyrrolidine.

When the substance formed has been purified, 114 g of N-[1-methyl 2-pyrrolidylmethyl] 2-methoxy 4-amino 5-methylsulphonyl benzamide is obtained (yield=62%-M.P.=190°-191° C.).

EXAMPLE IX

N-[1-ethyl 2-pyrrolidylmethyl] 2-methoxy 4-amino 5-methylsulphonyl benzamide

Following the same procedure as in Example I, 129 g of 2-methoxy 4-amino 5-methylsulphonyl benzoic acid dissolved in 526 ml of acetone, in the presence of 53 g of triethylamine, is treated with 57 g of ethyl chloroformate then with 81 g of 1-ethyl 2-aminomethyl pyrrolidine.

When the substance formed has been purified, 96 g of N-[1-ethyl 2-pyrrolidyl methyl] 2-methoxy 4-amino 5-methylsulphonyl benzamide is obtained (yield=52%-M.P.=151°-151.5° C.).

EXAMPLE X

N-oxide of N-(1-ethyl 2-pyrrolidylmethyl) 2-methoxy 4-amino 5-ethylsulphonyl benzamide

258.3 g of N-(1-ethyl 2-pyrrolidylmethyl) 2-methoxy 4-amino 5-ethylsulphonyl benzamide and 875 ml of absolute ethanol are placed in a 2 liter flask fitted with an agitator and a thermometer, and 142 ml of 110 vol. hydrogen peroxide is added with agitation. The mixture is heated to 45° C. for a few hours then cooled to 40° C., and 2 g of manganese dioxide is added in stages.

After the addition of vegetable black and filtration, the solvent is removed under vacuum. The residue obtained is dissolved in 200 ml of ethanol and 150 ml of acetone, then the solution is filtered and the filtrate poured into 2 l of sulphuric ether. The crystals formed are drained, washed with ether and dried.

140 g of N-oxide of N-(1-ethyl 2-pyrrolidylmethyl) 2-methoxy 4-amino 5-ethylsulphonyl benzamide is obtained (M.P.=190° C. with decomposition. Yield=52%).

EXAMPLE XI

N-oxide of N-(1-methyl 2-pyrrolidylmethyl) 2-methoxy 4-amino 5-ethylsulphonyl benzamide 248.5 g of N-(1-methyl 2-pyrrolidylmethyl) 2-methoxy 4-amino 5-ethylsulphonyl benzamide and 875 m of absolute ethanol are placed in a 2 liter flask fitted with an agitator and a thermometer, than 142 ml of 110 vol. hydrogen peroxide is added with agitation. The mixture is heated to 45° C. for a few hours then cooled to 40° C., and 2 g of manganese dioxide is added in stages.

The solution is filtered, after which the solvent is removed under vacuum and the residue dissolved in 500 ml of acetone. The crystals formed are drained and dried, then dissolved hot in 1 liter of ethanol.

Following the addition of 20 g of vegetable black, the solution is cooled then poured into 1 liter of sulphuric ether. The crystals formed are drained, washed and dried.

190 g of N-oxide of N-(1-methyl 2-pyrrolidylmethyl) 2-methoxy 4-amino 5-ethylsulphonyl benzamide is obtained (M.P.=200°-210° C. with decomposition-yield=73%).

EXAMPLE XII

N-(1-ethyl 2-pyrrolidylmethyl) 2-methoxy 4-amino 5-ethylsulphonyl benzamide

Composite anhydride of ethylbicarbonate and 2-methoxy 4-amino 5-ethylsulphonyl benzoic acid 77.7 g of 2-methoxy 4-amino 5-ethylsulphonyl benzoic acid and 500 ml of anhydrous dioxane are placed in a flask fitted with an agitator, a thermometer, a condenser and a dropping funnel, and 30.3 g of triethylamine is dripped in.

The mixture is cooled to 20° C. then 32.5 g of ethyl chloroformate is poured in drop by drop while the temperature is kept at 20° C.

The mixture is agitated and filtered, and the filtrate is evaporated under vacuum. The residue is dissolved in 500 ml of carbon tetrachloride then crystallisation is initiated by seeding.

The crystals which form when the mixture has cooled are filtered, washed and then dried.

74 g of anhydride is obtained (M.P.=77° C.-yield=74.5%).

N-(2,5-dichloropentyl) 2-methoxy 4-amino 5-ethylsulphonyl benzamide 4.33 g of 2,5-dichloropentylamine hydrochloride, 65 ml of dimethylformamide and 2.27 g of triethylamine are placed in a flask fitted with an agitator, a thermometer and a condenser, followed by 7.47 g of composite anhydride of ethylbicarbonate and 2-methoxy 4-amino 5-ethylsulphonyl benzoic acid.

The mixture is agitated for 1 hour at room temperature, after which 100 ml of water and 10 ml of hydrochloric acid are added.

The suspension obtained is evaporated dry under vacuum then the residue is dissolved in 100 ml of water.

The crystals formed are filtered, washed with water then dried in an oven at 50° C.

6.5 g of N-(2,5-dichloropentyl) 2-methoxy 4-amino 5-ethylsulphonyl benzamide is obtained (M.P.=109° C.-yield=73%).

N-(1-ethyl 2-pyrrolidyl methyl) 2-methoxy 4-amino 5-ethylsulphonyl benzamide 5.95 g of N-(2,5-dichloropentyl) 2-methoxy 4-amino 5-ethylsulphonyl benzamide and 22 ml of a 56% aqueous solution of ethyl amine are placed in a flask fitted with an agitator.

The mixture is agitated until the solids are completely dissolved, after which the solution is heated in an oven to 40°-45° C. until the reaction is over.

The solvent is evaporated, then the residue is treated with 100 ml of water and 5 ml of caustic soda solution.

After being twice extracted with methylene chloride, the organic phase is dried over magnesium sulphate and filtered, then the solvent is evaporated under vacuum.

The residue is dissolved at boiling point in 10 ml of acetone, then the crystals which form after cooling are filtered and dried in an oven at 50° C.

3 g of N-(1-ethyl 2-pyrrolidylmethyl) 2-methoxy 4-amino 5-ethylsulphonyl benzamide is obtained (M.P.=125° C.-yield=54%).

The substances according to the invention are used in the form of capsules, tablets, pills, in granular form or as an injectable solution; the preparation of these is known per se. It is possible to use substances which are inert relative to the compounds of the invention, such as levilite, alkali metal lauryl sulphates, saccharose, and the vehicles customarily used in medicinal preparations.

The compounds according to the invention may be administered in doses of 50 to 750 mg per day in one or more portions. The preferred doses are from 150 to 200 mg per day.

The following examples concern pharmaceutical preparations prepared in the conventional manner from compounds according to the invention.

EXAMPLE XIII—tablets

| | | |
|---|---|---|
| N-(1-ethyl 2-pyrrolidylmethyl) 2-methoxy 4-amino 5-ethylsulphonyl benzamide | 100 | mg |
| Dried starch (fecule) | 20 | mg |
| lactose | 100 | mg |
| methylcellulose 1500 cps | 1.5 | mg |
| levilite | 9.5 | mg |
| magnesium stearate | 4 | mg |

EXAMPLE XIV—tablets

| | | |
|---|---|---|
| N-(1-methyl 2-pyrrolidylmethyl) 2-methoxy 4-amino 5-ethylsulphonyl benzamide | 50 | mg |
| lactose | 50 | mg |
| dried starch | 10 | mg |
| methylcellulose 1500 cps | 0.687 | mg |
| 3% water | | |
| levilite | 6.803 | mg |
| magnesium stearate | 2.51 | mg |

EXAMPLE XV—injectable solution

| | | |
|---|---|---|
| N-(1-allyl 2-pyrrolidylmethyl) 2-methoxy 4-amino 5-ethylsulphonyl benzamide | 100 | mg |
| 1N hydrochloric acid | 0.26 | ml |

| -continued | | | |
|---|---|---|---|
| sodium chloride | | 8 | mg |
| water for injectable preparations | q.s. | 2 | ml |

To prepare the tablets, the selected compound is mixed with the starch and lactose by the method of successive dilutions; the mixture is granulated with methylcellulose. The levilite, magnesium stearate and talc are added to the granulated substances before proceeding to the compression stage.

It is possible to replace the methyl cellulose with any other appropriate granulating agent, such as ethyl cellulose, polyvinylpyrrolidone or starch paste.

The magnesium stearate may be replaced by stearic acid. To prepare injectable solutions, it is possible to dissolve the compound according to the invention in the following acids: hydrochloric, levulinic, gluconic or glucoheptonic.

The solution, prepared under sterile conditions, is made isotonic by an alkali metal chloride such as sodium chloride, then preservatives are added. It is equally possible to prepare the same solution without adding any preservatives: the ampoule is filled in a nitrogen atmosphere and sterilised for ½ hour at 100° C.

We claim:

1. A pharmaceutical composition having antiemetic or antiserotonin activity comprising an effective amount of a compound selected from the group consisting of 4-amino-5-alkylsulphonylortho-anisamides having the formula:

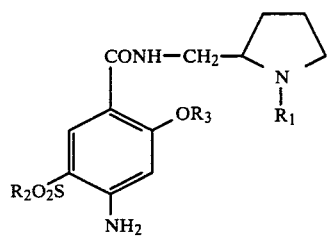

wherein:
$R_1$ is lower alkyl of 1 to 5 carbon atoms or lower alkenyl of 2 to 5 carbon atoms and $R_2$ and $R_3$ are lower alkyl of 1 to 5 carbon atoms,
the N-oxides of said anisamides, the addition salts of said derivatives with pharmacologically acceptable acids, the quaternary ammonium salts of said derivatives and the levorotatory and dextrorotatory optical isomers of all of the foregoing compounds, and a pharmaceutically acceptable carrier.

2. A method of treating patients having need of an antiemetic active substance which comprises administering to said patient an effective amount of a compound selected from the group consisting of 4-amino-5-alkylsulphonylortho-anisamides having the formula:

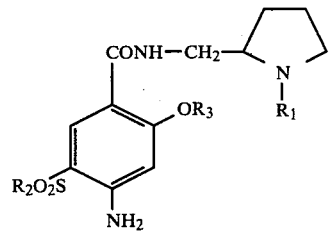

wherein:
$R_1$ is lower alkyl of 1 to 5 carbon atoms or lower alkenyl of 2 to 5 carbon atoms and $R_2$ and $R_3$ are lower alkyl of 1 to 5 carbon atoms,
the N-oxides of said anisamides, the addition salts of said derivatives with pharmacologically acceptable acids, the quaternary ammonium salts of said derivatives and the levorotatory and dextrorotatory optical isomers of all of the foregoing compounds.

3. A method of treating patients having need of an antiserotonin active composition comprising administering to said patient an effective amount of a compound selected from the group consisting of 4-amino-5-alkylsulphonylortho-anisamides having the formula:

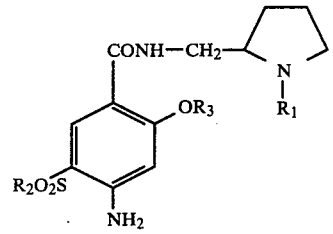

wherein:
$R_1$ is lower alkyl of 1 to 5 carbon atoms or lower alkenyl of 2 to 5 carbon atoms and $R_2$ and $R_3$ are lower alkyl of 1 to 5 carbon atoms,
the N-oxides of said anisamides, the addition salts of said derivatives with pharmacologically acceptable acids, the quaternary ammonium salts of said derivatives and the levorotatory and dextrorotatory optical isomers of all of the foregoing compounds.

* * * * *